United States Patent
Pieniak et al.

[11] Patent Number: 6,123,694
[45] Date of Patent: *Sep. 26, 2000

[54] DISPOSABLE ABSORBENT ARTICLE WITH UNITARY LEG GATHERS

[75] Inventors: Heinz A. Pieniak, Des Moines; Gloria Huffman, Kent; Jill M. Riley, Auburn, all of Wash.

[73] Assignee: Paragon Trade Brands, Norcross, Ga.

[ * ] Notice: This patent issued on a continued prosecution application filed under 37 CFR 1.53(d), and is subject to the twenty year patent term provisions of 35 U.S.C. 154(a)(2).

[21] Appl. No.: 08/853,761

[22] Filed: May 9, 1997

[51] Int. Cl.⁷ ..................................................... A61F 13/15
[52] U.S. Cl. .................................. 604/385.2; 604/385.1
[58] Field of Search .............................. 604/385.1, 385.2, 604/386, 387

[56] References Cited

U.S. PATENT DOCUMENTS

| | | |
|---|---|---|
| Re. 33,106 | 11/1989 | Beckestrom . |
| 3,860,003 | 1/1975 | Buell . |
| 4,300,562 | 11/1981 | Pieniak .................. 604/385.2 |
| 4,695,278 | 9/1987 | Lawson . |
| 4,704,116 | 11/1987 | Enloe . |
| 4,795,454 | 1/1989 | Dragoo . |
| 4,808,178 | 2/1989 | Aziz et al. . |
| 4,822,435 | 4/1989 | Igaue et al. . |
| 4,900,317 | 2/1990 | Buell . |
| 5,021,051 | 6/1991 | Hiuke .................... 604/385.2 |
| 5,061,261 | 10/1991 | Suzuki et al. . |
| 5,064,489 | 11/1991 | Ujimoto et al. . |
| 5,110,386 | 5/1992 | Ochi et al. . |
| 5,114,420 | 5/1992 | Igaue et al. . |
| 5,167,653 | 12/1992 | Igaue et al. . |
| 5,188,627 | 2/1993 | Igaue et al. . |
| 5,246,432 | 9/1993 | Suzuki et al. . |
| 5,275,590 | 1/1994 | Huffman et al. . |
| 5,292,316 | 3/1994 | Suzuki . |
| 5,397,318 | 3/1995 | Dreier .................... 604/385.2 |
| 5,540,671 | 7/1996 | Dreier . |
| 5,558,660 | 9/1996 | Drier . |
| 5,569,227 | 10/1996 | Vandenoortele et al. . |
| 5,569,234 | 10/1996 | Buell et al. . |
| 5,599,334 | 2/1997 | Johnston et al. . |

(List continued on next page.)

FOREIGN PATENT DOCUMENTS

| | | |
|---|---|---|
| 866527 | 10/1978 | Belgium . |
| 518044 | 12/1992 | European Pat. Off. ............ 604/385.2 |
| 41-18359 | 8/1966 | Japan . |
| 301555 | 11/1989 | Japan . |
| 328020 | 12/1989 | Japan . |
| 4-92665 | 3/1992 | Japan . |
| 4-322646 | 11/1992 | Japan . |
| 4-325153 | 11/1992 | Japan ................. 604/385.2 |
| 5-49658 | 3/1993 | Japan . |
| 6-47073 | 2/1994 | Japan . |

*Primary Examiner*—Mark O. Polutta
*Attorney, Agent, or Firm*—Hunton & Williams

[57] ABSTRACT

A disposable absorbent article, which can be configured as a disposable diaper, a panty-type garment, or an adult incontinent product, includes a backsheet, an absorbent panel positioned on top of the backsheet, and a liquid permeable topsheet positioned on top of the absorbent panel. A pair of longitudinally extending, elasticized unitary leg gather assemblies are positioned on respective opposite sides of a longitudinal centerline of the article. Each leg gather assembly includes an outer sleeve having an upstanding portion within which are positioned at least two, and preferably at least three, elastically contractible elastic elements which effect conformance of the leg gather assemblies with a wearer for desired containment. A lowermost one of the elastic elements in each leg gather assembly exerts a relatively greater elastic gathering force than the other elastic elements to effect gathering of associated components of the article, thus enhancing fit. Apart from the leg gather assemblies, side marginal portions of the absorbent article are non-elasticized for enhanced aesthetics, and for facilitating efficient, high-speed manufacture.

17 Claims, 4 Drawing Sheets

U.S. PATENT DOCUMENTS

| | | |
|---|---|---|
| 5,601,547 | 2/1997 | Kato et al. . |
| 5,607,416 | 3/1997 | Yamamoto et al. . |
| 5,613,961 | 3/1997 | DiPalma et al. . |
| 5,643,243 | 7/1997 | Klemp .................................. 604/385.2 |
| 5,674,213 | 10/1997 | Sauer .................................. 604/385.2 |
| 5,827,859 | 10/1998 | Laux et al. ........................... 604/385.2 |
| 5,876,392 | 3/1999 | Hisada ................................. 604/385.2 |

DISPOSABLE ABSORBENT ARTICLE WITH UNITARY LEG GATHERS

TECHNICAL FIELD

The present invention relates generally to a disposable absorbent article which can be configured as a disposable diaper, training pants, or adult incontinent product, and more particularly to a disposable absorbent article having a pair of elasticized, upstanding unitary leg gather assemblies configured for enhanced containment and efficient high-speed manufacture.

BACKGROUND OF THE INVENTION

Disposable absorbent articles, such as disposable diapers and disposable pant-type garments (sometimes referred to as training pants) have found widespread acceptance for infant care. Garments of this nature are typically configured for a single use, with an absorbent panel or core of the construction ordinarily provided in an integrated structure including a liquid-pervious topsheet or facing layer, and a backsheet or backing layer having at least a portion which is liquid impervious. Adhesive coated fastening tabs, or hook-and-loop fasteners are typically provided on disposable diapers, while pant-type garments include side seams which can be readily torn for removal of the garment if soiled. Absorbent articles of the above nature are not only suitable for infants, but can be appropriately sized and configured for incontinence use by adults.

Commonly assigned U.S. Pat. No. 5,403,301 discloses a disposable absorbent garment of the type suitable for infant care and for use by incontinent adults. In order to enhance the containment characteristics of the absorbent article disclosed in this patent, the construction includes elastication at laterally opposite side margins of the construction, thereby forming leg-encircling elasticized regions. Containment is further enhanced by the provision of a pair of upstanding, standing gather elements, respectively positioned generally inwardly of the leg-encircling elasticized regions. This patent is hereby incorporated by reference.

Experience has shown that, in a disposable absorbent garment of the type disclosed in the above patent, the standing leg gather elements of the construction contribute substantially to the containment characteristics of the article. Accordingly, the present invention is directed to a disposable absorbent article having unitary, elasticized leg gather assemblies specifically configured for maximizing containment characteristics, with side marginal portions of the article being otherwise non-elasticized for more economical manufacture, including enhanced efficiency during high-speed fabrication.

SUMMARY OF THE INVENTION

A disposable absorbent article embodying the principles of the present invention can be configured as a disposable diaper, or a pant-type garment, for infants or small children, or can be appropriately sized and configured for use by incontinent adults. For enhancing the containment and fit characteristics of the article, the construction includes a pair of longitudinally extending, generally upstanding elasticized leg gather assemblies, which are preferably each provided with at least two, and more preferably at least three, elastically contractible elastic elements. The elastic elements are positioned within an outer sleeve of each leg gather assembly for distributing elastic contraction forces generated by the elastic elements over a substantial portion of the vertical extent of each leg gather assembly. Preferably, at least one of the elastic elements of each leg gather assembly is positioned in sufficiently closely spaced relationship to associated components of the article for gathering the article for enhanced fit and aesthetic appeal.

In accordance with the illustrated embodiment, the present disposable absorbent article includes a backsheet preferably having at least a portion which is liquid impervious, and an absorbent panel positioned on top of the backsheet. The absorbent panel preferably comprises absorbent material such as comminuted wood pulp (wood fluff) with superabsorbent polymer distributed therein.

The article further includes a liquid pervious topsheet positioned on top of the absorbent panel, with the topsheet being positionable generally adjacent to a wearer during use of the article.

In accordance with the present invention, a pair of longitudinally extending, elasticized leg gather assemblies are positioned on respective opposite sides of a longitudinal centerline of the article. Each leg gather assembly includes an outer sleeve joined to the topsheet of the article, and at least two, and preferably three or more, elastically contractible elastic elements. The elastic elements are positioned in spaced apart relationship within an upstanding portion of the outer sleeve of each leg gather assembly, in a manner which desirably acts to distribute the elastic contraction forces generated by the elements along a substantial portion of the vertical extent of each leg gather assembly. To this end, it is preferred that at least one elastic element be positioned within an upper half of the upstanding portion of each outer sleeve, and at least one elastic element be positioned with lower half of the upstanding portion of each outer sleeve. While elastication of the article is effected by the provision of the elastic elements of the leg gather assemblies, it is presently preferred that the side marginal portions of the article are not otherwise elasticized. The resultant construction not only provides the desired containment and fit characteristics, with enhanced aesthetic appeal, but also facilitates high-speed manufacture for economical use.

In accordance with the illustrated embodiment, each leg gather assembly includes at least three substantially evenly spaced apart elastic elements, and more preferably four spaced apart elastic elements. In order to effect gathering of the backsheet of the article, as well as the associated absorbent panel, for the desired fit, one of the elastic elements in each leg gather assembly spaced furthest from a free edge portion thereof can be configured to exert a greater elastic gathering force on the respective outer sleeve than the other ones of the elastic elements. This desired differential elastic gathering effect can be created by providing the one elastic element with a greater modulus of elasticity, such by configuring it to have a greater untensioned cross-sectional area than the other ones of the elastic elements. The one of the elastic elements exerting the greater gathering force can alternatively, or in addition, be subjected to greater elongation than the other ones of the elastic elements.

In the preferred form, the outer sleeve of each leg gather assembly comprises hydrophobic nonwoven fabric, and may be configured as a composite including nonwoven fabric and an associated plastic film layer. In the illustrated form, the outer sleeve of each leg gather assembly includes a base portion, which base portion may be joined to a respective lateral edge of the topsheet and extend laterally outwardly therefrom to a respective side edge of the article. Alternatively, the topsheet can be configured to extend laterally outwardly beneath said leg gather assemblies to the side edges of the absorbent article, with each leg gather assembly having a ribbon-like configuration, respectively positioned on top of the topsheet of the article.

As noted, it is contemplated that the elastic elements of each leg gather assembly be positioned for distributing the elastic contraction forces generated thereby along a substantial portion of the vertical extent of each leg gather assembly, with at least one elastic element is positioned within an upper half of an upstanding portion of the outer sleeve of each leg gather assembly, with at least one elastic element positioned within a lower half of the upstanding portion of each outer sleeve. Preferably, the elastic element positioned within the lower half of the upstanding portion of the outer sleeve exerts a greater elastic gathering force on the outer sleeve than one of the elastic elements in the upper half of the upstanding portion, with the elastic element positioned within the lower half of the upstanding portion optionally spaced throughout its extent from the associated backsheet of the article.

Other features and advantages of the present invention will become readily apparent from the following detailed description, the accompanying drawings, and the appended claims.

DETAILED DESCRIPTION

Figure 1:
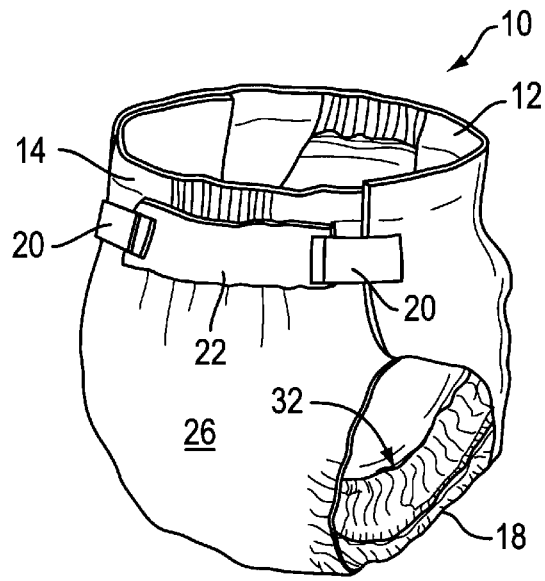
FIG. 1 is a perspective view of a disposable absorbent article, configured as a disposable diaper, embodying the principles of the present invention generally as it appears when being worn.

While the present invention is susceptible of embodiment in various forms, there is shown in the drawings and will hereinafter be described presently preferred embodiments, with the understanding that the present disclosure is to be considered as an exemplification of the invention, and is not intended to limit the invention to the specific embodiment illustrated.

With reference now to the drawings, therein is illustrated a disposable absorbent article 10, illustrated as a disposable diaper, embodying the principles of the present invention. As used in the present disclosure, the term "diaper" is intended to refer to an absorbent article or garment which is worn by an individual for absorbing urine and/or fecal matter. It is understood that garments embodying the principles of the present invention can be appropriately sized for use by infants and children, and can further be sized for use by incontinent adults. While the absorbent article 10 has been illustrated as a disposable diaper, including a fastening arrangement for fitting the article about a wearer so as to define a waist opening and a pair of leg openings, it will be understood that an article embodying the principles of the present invention can be configured as a pant-type garment (sometimes referred to as training pants, or a pull-up diaper) for use by infants or small children. In such a construction, the article is formed with side seams, thus defining a waist opening and a pair of leg openings, with the side seams being readily torn to facilitate removal of the garment, if soiled.

Figure 2:
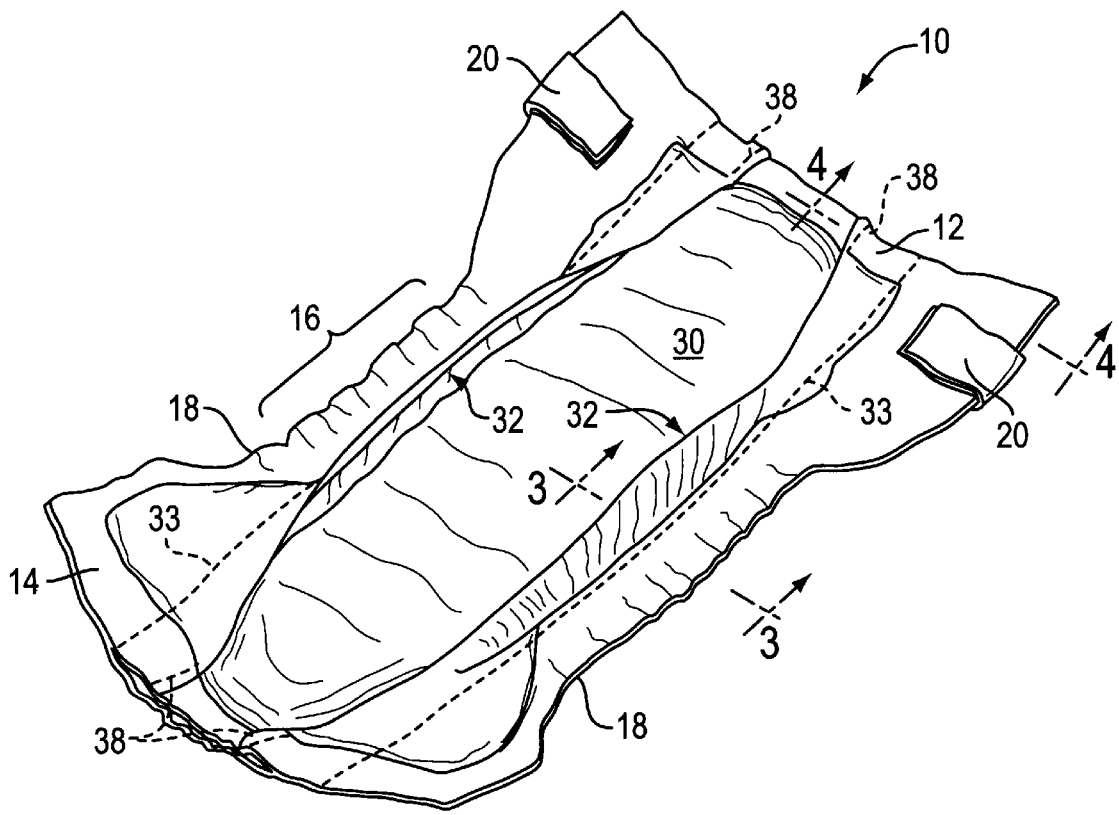
FIG. 2 is a top perspective view of the present absorbent article generally in a form prior to use.

With particular reference to FIG. 2, the absorbent article 10 includes a rear waist portion 12, a front waist portion 14, and a crotch area 16 extending between the front and rear waist portions. The crotch area of the garment generally corresponds to that portion which is positioned between the legs of a wearer during use, and as used herein, comprises between about one-third and three-fourths of the longitudinally central portion of the garment.

For enhanced fit and comfort, the disposable absorbent article 10 has a generally I-shaped, contoured configuration, with the crotch area 16 being relatively narrow by virtue of the formation of leg cut-outs 18 at each of the side margins of the garment.

Convenient securement of the absorbent article 10 to a wearer is facilitated by the provision of a pair of adhesive-coated tape tabs 20 at respective opposite sides of the rear waist portion 12 of the garment. The tape tabs 20 are positioned for securement to the outside surface of the front waist portion 14, as illustrated in FIG. 1, and to this end, a tape landing zone 22 is preferably provided. Tape landing zone 22 typically comprises a strip of polymeric sheet material to which the tape tabs can be securely yet removably applied, with the landing zone 22 desirably acting to reinforce the front outside surface of the garment so that removal and reapplication of the tape tabs does not damage the article. While the provision of adhesive-coated tape tabs is illustrated, it will be understood that a suitable fastening arrangement can alternately be provided by the provision of hook-and-loop type fasteners, with tape tabs such as 20 provided with suitable hook material, and with the region generally corresponding to tape landing zone 22 provided with suitable loop material.

Figure 3:
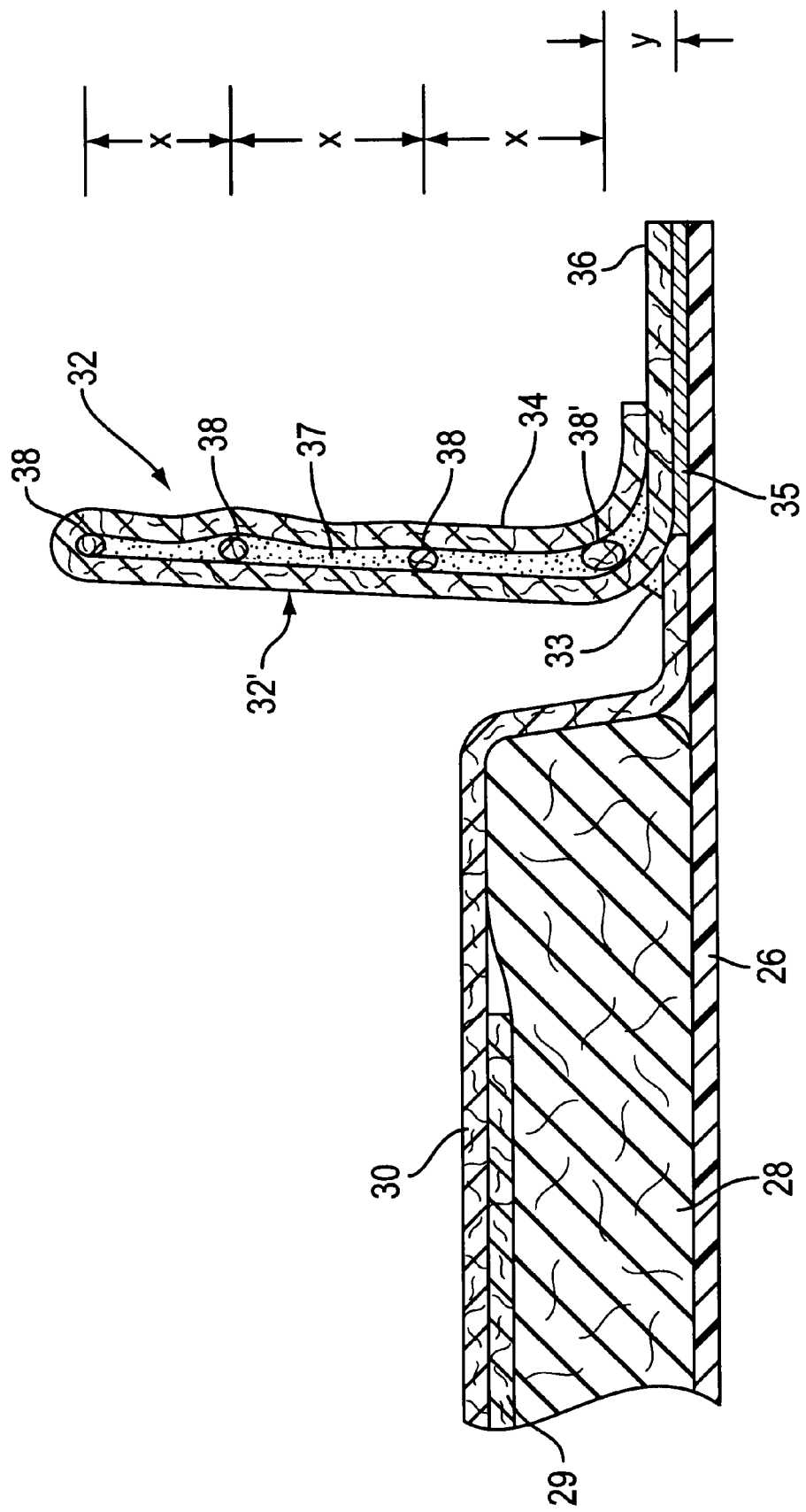
FIG. 3 is a fragmentary, cross-sectional view taken generally along lines 3—3 of FIG. 2.
Figure 4:
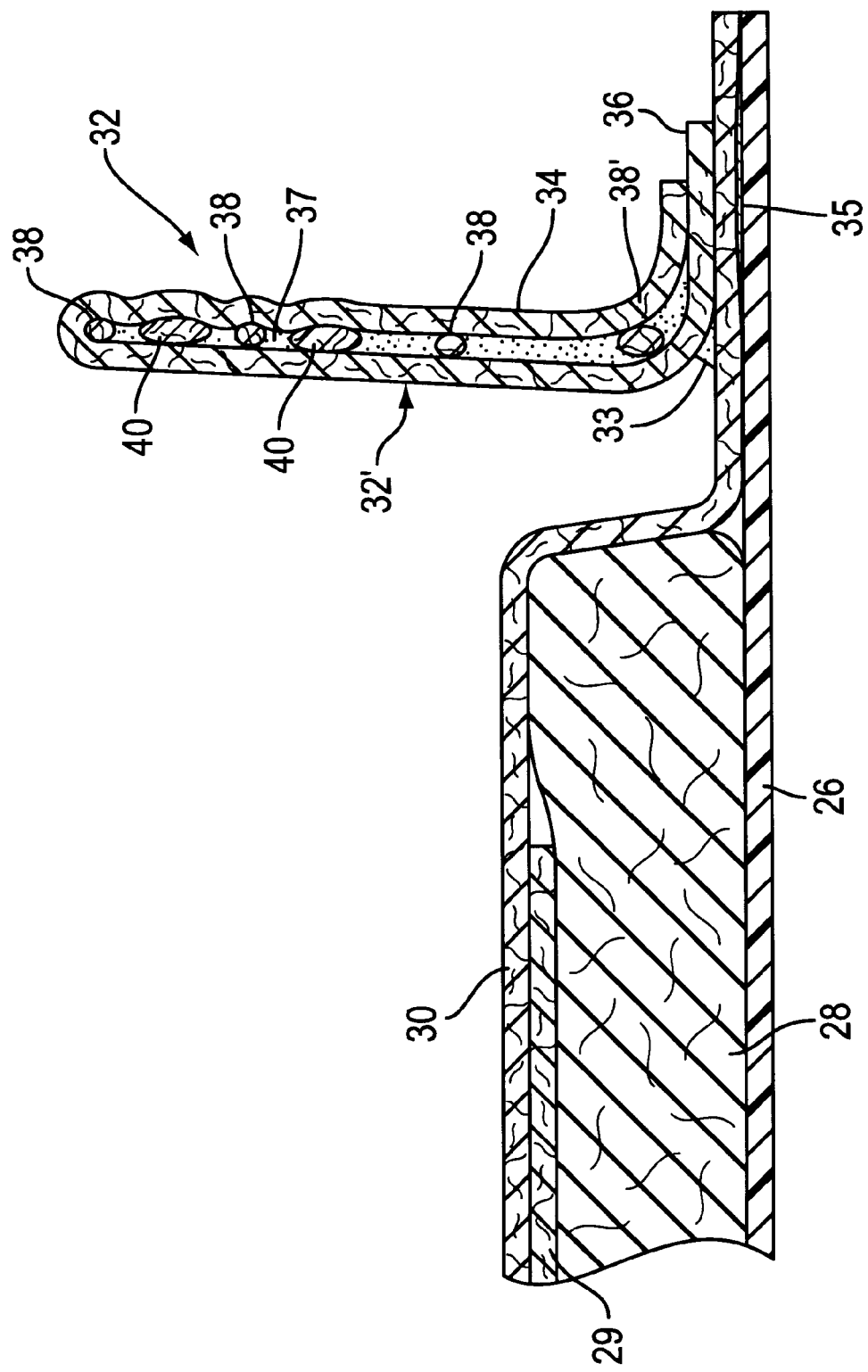
FIG. 4 is a fragmentary, cross-sectional view similar to FIG. 3 illustrating alternative embodiments of the present invention.
Figure 5:
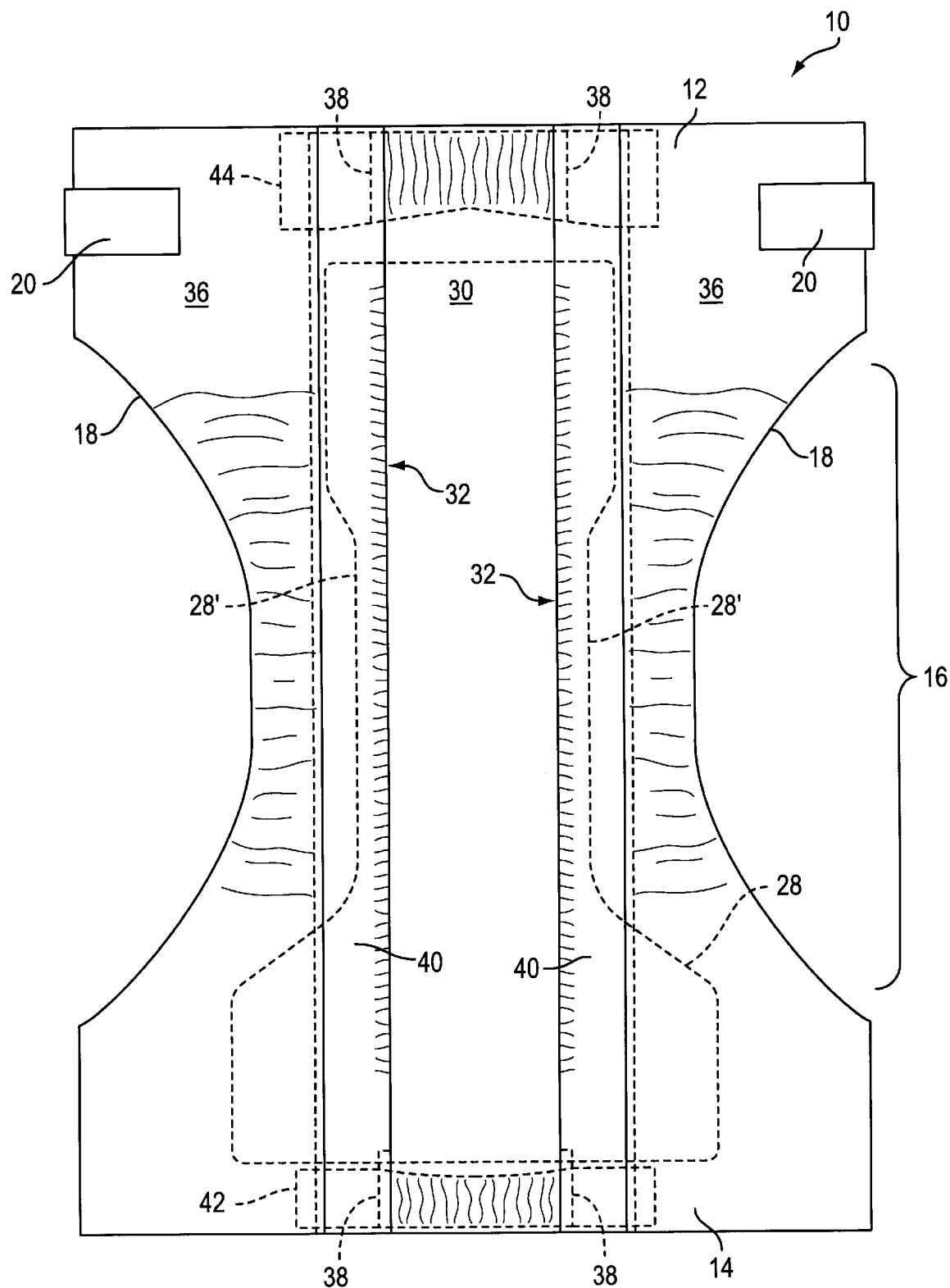
FIG. 5 is a top plan view of the present invention.

With reference to FIGS. 2, 3, and 4, the absorbent article 10 includes a backsheet 26 which generally defines the outer surface of the garment. The entire backsheet 26 can be formed from suitable polymeric film material, such as polyethylene sheet having a thickness on the order of 0.0005 to 0.001 inches. Polyethylene terephthalate sheet material having a thickness of approximately 0.0005 to 0.001 inches may alternately be employed. If desired, the backsheet 26 can be configured as a composite of an outer nonwoven fabric layer and an inner polymeric film layer. In such an arrangement, the inner polymeric film layer may be coextensive with the outer nonwoven fabric layer, or can be configured to extend generally beneath the absorbent panel of the article (to be described) but dimensioned smaller than the associated outer nonwoven fabric layer. In such a construction, laterally extending "ear portions" of the backsheet 26, generally corresponding to the four corner regions thereof, can exhibit desired breathability (by virtue of the absence of polymeric film material in these areas) for enhanced comfort by the wearer.

The absorbent article 10 includes an absorbent panel 28 preferably defining leg cut-outs 28', positioned on top of the backsheet 26. The absorbent panel preferably comprises an absorbent matrix including comminuted wood pulp, sometimes referred to a wood fluff, and superabsorbent material, which may comprise superabsorbent polymers or the like. Absorbent matrices comprising blends and/or layers of absorbent material can be employed. If desired, the superabsorbent material may be concentrated in specifically selected regions of the absorbent panel.

In the preferred embodiment, a liquid distributing transfer layer 29 is positioned on top of the absorbent panel 28. The transfer layer preferably comprises a low basis weight nonwoven fabric layer, which in a presently preferred form, comprises thermally bonded bicomponent fibers of polyester and polypropylene, having a basis weight of 40 grams per square meter. Suitable material can be obtained from Fiberweb North America, Inc., under the product designation DFPN156.

Absorbent article 10 includes a topsheet 30 positioned on top of the absorbent panel 28. The topsheet 30 can be configured in accordance with the illustrated embodiment, to have a longitudinal extent substantially corresponding to the length of the article 10, and a transverse dimension such that the topsheet 30 has side edges spaced inwardly of respective side edges of the article 10. In this construction, each of the side edges of the topsheet 30 is respectively joined to a unitary leg gather assembly, designated 32, in accordance with the principles of the present invention. The topsheet is joined to each leg gather assembly 32 by a respective bond 33, which may comprise sonic bonding or suitable adhesive. Alternatively, as illustrated in FIG. 4, the topsheet 30 can extend beneath each of the leg gather assemblies 32 laterally outwardly to the side edges of the article 10, and joined to the backsheet 26 with suitable adhesive of sonic bonding 35 with each leg gather assembly thus having a ribbon-like configuration.

Each of the longitudinally extending leg gather assemblies 32 is elasticized in a specifically configured arrangement to provide the desired containment and fit characteristics for the disposable absorbent article 10. Specifically, each leg gather assembly 32 includes an outer sleeve 32' preferably comprising nonwoven fabric having an upstanding portion 34, and a laterally extending base portion 36. In the illustrated embodiment, the outer sleeve of each leg gather assembly is joined to a respective side edge of topsheet 30 at bond 33 so that the base portion 36 extends laterally outwardly from the topsheet to the respective side edge of the absorbent article and is joined to the backsheet 26 with suitable adhesive or sonic bonding 35. However, the outer sleeve can be configured such that the base portion extends laterally inwardly. If desired, each leg gather assembly 32 can be arranged to have a generally inverted T-shaped configuration, wherein the base portion 36 extends beneath, and inwardly and outwardly of, the associated upstanding portion 34. While the free edges of the material forming the outer sleeve are illustrated as being positioned at the base portion 36, these free edges can be otherwise positioned, such as at the uppermost edge of the outer sleeve 32'.

The upstanding portion 34 of the outer sleeve 32' of each leg gather assembly includes an overturned free edge to provide the desired sleeve-like configuration for each leg gather assembly within which the plural elastic elements of each leg gather assembly are positioned. The outer sleeve of each leg gather assembly is secured in this overturned position by suitable bonding, such as by the application of spray adhesive 37, or by the provision of suitable sonic bonding. Elastication of the outer sleeve of each leg gather assembly results in the upstanding portion 34 thereof to assume a generally upstanding vertical orientation with respect to the associated topsheet 30. By this arrangement, each leg gather assembly tends to extend generally toward the perineal region of the wearer, generally toward what is sometimes referred to as the thigh crease.

In accordance with the present invention, enhanced containment and fit are provided by the provision of at least two, and preferably three or more elastic elements within the outer sleeve of each of the leg gather assemblies 32. In a presently preferred embodiment, three, and preferably four, evenly spaced apart elastic elements 38, 38' are provided within the upstanding portion 34 of the outer sleeve of each leg gather assembly 32. In a current embodiment, the elastic elements are evenly spaced apart by a dimension "x" of about 11 mm, with the lowermost elastic 38' spaced throughout its extent from the backsheet 26 by a dimension "y" of about 2 mm.

As noted above, the leg gather assemblies 32 of the present disposable absorbent article have been particularly configured for enhanced containment and fit, thereby permitting the side marginal portions of the article to otherwise be non-elasticized. To this end, at least two of the elastic elements are provided within the outer sleeve of each leg gather assembly, with at least one elastic element provided in an upper half of each upstanding portion 34 of the respective outer sleeve, and at least one elastic element positioned within the lower half of the upstanding portion of each outer sleeve. In order to create the desired fit characteristics, one of the elastic elements positioned within the lower half of the upstanding portion of the outer sleeve exerts a greater elastic gathering force on the outer sleeve than one of the elastic elements in the upper half of the upstanding portion. In accordance with the illustrated embodiment, one of the elastic elements exerting the greater gathering force, designated 38', is positioned within the lower half of the upstanding portion 34 of outer sleeve 32', and can be positioned in spaced relationship from the backsheet 26 throughout its extent.

Thus, the elastic element 38' in each leg gather assembly 32 spaced furthest from a free edge portion of the outer sleeve 32' exerts a greater elastic gathering force on the respective outer sleeve than the other ones of the elastic elements.

By the provision of at least three substantially evenly spaced apart elastic elements 38, 38' positioned within the respective outer sleeve 32', elastic contraction forces generated by the elastic elements are distributed along a substantial portion of the vertical extent of each leg gather assembly. By the preferred provision of a lowermost one of the elastic elements in a configuration so as to exert a greater elastic gathering force than the other ones of the elements, gathering of the backsheet 26, and the associated absorbent panel 28, is effected for enhanced fit of the article, thus enhancing the aesthetics of the article. Enhanced containment is also achieved by this enhanced fit, since it permits the elasticized upstanding portion of each leg gather assembly 32 to conform to the wearer as intended.

As noted, the preferred embodiment of the present invention is configured such that the side marginal portions of the article, i.e., those portions of the construction disposed generally laterally outwardly of bonds 33, are non-elasticized, other than by the elastication provided by the elastic elements 38, 38' of each leg gather assembly 32. As such, the base portion 36 of the outer sleeve of each leg gather assembly is non-elasticized, except by any elastication provided by the spaced apart elastic elements 38, 38'.

Configuring elastic element 38' for exerting a greater elastic gathering force on the outer sleeve of each leg gather assembly 32 can be effected in any of a variety of ways. If desired, the elastic element 38' can have an untensioned cross-sectional area greater than the other elastic elements 38, and thus exhibit a greater modulus of elasticity. Elastic element 38' can comprise material which is different than the other elastic elements 38, and thus be configured to exhibit a greater modulus of elasticity. If desired, the elastic element 38' can be subjected to greater elongation than the other ones of the elastic elements, and thus be configured to create a greater elastic gathering force than the other elements, even if exhibiting an untensioned cross-sectional area which is the same as the other elements.

In the preferred form, the outer sleeve of each of the leg gather assemblies 32 preferably comprises hydrophobic nonwoven fabric, thereby resisting the passage of liquid therethrough. A suitable fabric can comprise spunbonded polypropylene nonwoven fabric having a basis weight in the range of about 0.03 to 0.8 ounces per square yard and a bond area in the range of 7% to 20%, with a basis weight of about 0.5 to 0.6 ounces per square yard, and an 18% bond area being particularly preferred. When untreated, this material exhibits the desired degree of hydrophobicity. One commercially available material of this type is available from Fiberweb of America, Greenville, S.C., under the product designation Unicorn Celestra.

The topsheet 30 may also comprise a polypropylene nonwoven fabric having a basis weight and bond areas described above for the outer sleeves of the leg gather assemblies 32. While the liquid permeability characteristics of the topsheet 30 can be selectively varied while keeping with the principles disclosed herein, it is presently preferred that the topsheet 30 be selected to exhibit significantly greater hydrophilicity, and thus, greater liquid permeability, than the outer sleeves 32' of the leg gather assemblies 32. To this end, polypropylene nonwoven material such as described above is ordinarily treated with a surfactant to achieve the desired hydrophilicity. Alternatively, a hydrophobic fabric having apertures to permit liquid passage therethrough may be employed.

In the preferred form, the upstanding portion 34 of each of the leg gather assemblies 32 is partially secured to the top surface of the associated topsheet 30. In particular, at least one longitudinal end of the upstanding portion 34 of the outer sleeve of each leg gather assembly is secured inwardly to the topsheet, such as by suitable adhesive or sonic bonding, as indicated at 39. Most preferably, approximately 10% of the total length of each leg gather assembly 32 is secured inwardly to the associated topsheet at each end of each leg gather assembly (i.e., 20% of the entire length is attached to the topsheet). Additional design features are preferred in configuring the present disposable absorbent article 10 for the desired containment and fit characteristics. It is believed that the elastically contractible gathering force asserted from each leg gather assembly on the associated diaper components, including the backsheet 26, should effect contraction from a fully elongated length in the range from about 20% to 50%. This is preferably achieved by positioning the lowermost elastic element 38' no more than about 0.25 inches from the backsheet 26. The disposition of each leg gather assembly 32 with respect to the associated absorbent panel 28 is such that the base portion 36 of each leg gather assembly is preferably no more than about 1 inch away from the narrowest portion of the absorbent panel, with this base portion being preferably positioned no more than about 1 inch inwardly from the respective side edge of the article.

While the embodiment of the present disposable absorbent article heretofore described includes leg gather assemblies 32 principally comprising an outer sleeve component, and plural elastic elements positioned therein, it can be beneficial to increase the bulk of each leg gather assembly by disposition of soft cushioning material (preferably substantially non-absorbent) within the outer sleeve of each leg gather assembly. Such bulk-increasing material, such as indicated generally at 40 in FIG. 4, can take any of a variety of forms, such as rayon sliver, polypropylene batting material, crimped polyester/polypropylene tow, suitable foam material, suitable nonwoven fabric material, or combinations thereof. Waste material typically generated during disposable absorbent article manufacture (such as at cut-out regions or the like) can be shredded and positioned within the outer sleeve of each leg gather assembly 32 for increasing the bulk thereof.

While leg gather assemblies 32 have been illustrated as being generally linear and in parallel relationship to each other and to the centerline of the disposable article 10, it is within the purview of the present invention to position the leg gather assemblies in a curved or otherwise non-parallel configuration. For example, the ribbon-like leg gather assemblies 32 illustrated in FIG. 4 can be formed to each have a length preferably at least 10% greater than that of the absorbent article, and then attached to the article to each define a curved configuration by virtue of the "extra material" of each leg gather assembly.

In accordance with the illustrated embodiment, front and rear waist elastic elements 42, 44, such as comprising elastic foam material, are preferably provided between the backsheet 26 and the topsheet 30 for enhanced fit, containment, and comfort.

From the foregoing, it will be observed that numerous modifications and variations can be effected without departing from the true spirit and scope of the novel concept of the present invention. It is to be understood that no limitation with respect to the specific embodiments illustrated herein is intended or should be inferred. The disclosure is intended to cover, by the appended claims, all such modifications as fall within the scope of the claims.

What is claimed is:

1. A disposable absorbent article, comprising:
   a backsheet;
   an absorbent panel positioned on top of said backsheet;
   a topsheet positioned on top of said absorbent panel;
   a pair of longitudinally extending, elasticized leg gather assemblies positioned on respective opposite sides of a longitudinal centerline of said article, each said leg gather assembly including an outer sleeve joined to said topsheet; and
   at least three substantially, evenly spaced apart elastic elements for distributing elastic contraction forces generated by said elastic elements along a substantial portion of the vertical extent of each leg gather assembly for conforming each leg gather assembly to a wearer for enhanced containment wherein one of said elastic elements in each leg gather assembly spaced furthest from a free edge portion thereof exerts a greater elastic gathering force on the respective outer sleeve than the other ones of the elastic elements.

2. A disposable absorbent article in accordance with claim 1, wherein
   said sleeve portion of each said leg gather assembly includes a base portion extending laterally outwardly from said topsheet to respective side edge of said absorbent article.

3. A disposable absorbent article in accordance with claim 1, wherein
   said topsheet extends laterally outwardly beneath said leg gather assemblies to side edges of said absorbent article.

4. A disposable absorbent article in accordance with claim 1, wherein
   said one elastic element of each leg gather assembly has a greater untensioned cross-sectional area than said other ones of said elastic elements.

5. A disposable absorbent article in accordance with claim 1, wherein
said one elastic element of each leg gather assembly is subjected to greater elongation than said other ones of said elastic elements.

6. A disposable absorbent article in accordance with claim 1, wherein
said outer sleeve of each said leg gather assembly comprises hydrophobic nonwoven fabric.

7. A disposable absorbent article, comprising:

a backsheet;

an absorbent panel positioned on top of said backsheet;

a topsheet positioned on top of said absorbent panel; and a pair of longitudinally extending, elasticized leg gather assemblies positioned on respective opposite sides of a longitudinal centerline of said article, each said leg gather assembly including an outer sleeve comprising hydrophobic nonwoven fabric having a base portion joined to a respective lateral edge of said topsheet and extending laterally outwardly therefrom to a respective side edge of said absorbent article;

each said leg gather assembly including at least two spaced apart elastic elements respectively positioned within upper and lower halves of an upstanding portion of said outer sleeve and wherein one of said elastic elements positioned within the lower half of the upstanding portion of the outer sleeve exerts a greater elastic gathering force on the outer sleeve than one of the elastic elements in the upper half of the upstanding portion.

8. A disposable absorbent article in accordance with claim 7, wherein
said one of said elastic elements positioned within the lower half of the upstanding portion of the other sleeve is spaced throughout its extent from said backsheet.

9. A disposable absorbent article in accordance with claim 7, wherein
at least one longitudinal end of the upstanding portion of the outer sleeve of each said leg gather assembly is secured inwardly to said topsheet.

10. A disposable absorbent article in accordance with claim 7, wherein
said outer sleeve of each said leg gather assembly comprises a composite of nonwoven fabric and plastic film.

11. A disposable absorbent article in accordance with claim 7, wherein
said leg gather assemblies are parallel to each other.

12. A disposable absorbent article comprising:

a backsheet;

an absorbent panel positioned on top of said backsheet;

a topsheet positioned on top of said absorbent panel; and a pair of longitudinally extending, elasticized leg gather assemblies positioned on respective opposite sides of a longitudinal centerline of said article, each said leg gather assembly including an outer sleeve comprising a hydrophobic nonwoven fabric having a base portion joined to a respective lateral edge of said topsheet and extending laterally outwardly therefrom to a respective side edge of said absorbent article, each said leg gather assembly including at least three spaced apart elastic elements for conforming each leg gather assembly to a wearer for enhanced containment, at least one of said elastic elements of each leg gather assembly being positioned within a lower half of an upstanding portion of said outer sleeve and exerting a greater elastic gathering force than at least one of the other elastic elements positioned within an upper half of said upstanding portion.

13. A disposable absorbent article in accordance with claim 12, wherein
said outer sleeve of each said leg gather assembly comprises a composite of nonwoven fabric and plastic film.

14. A disposable absorbent article in accordance with claim 12, wherein
each said leg gather assembly includes four substantially evenly spaced elastic elements for distributing elastic contraction forces generated by said elastic elements along a substantial portion of the vertical extent of the upstanding portion of the outer sleeve of each leg gather assembly.

15. A disposable absorbent article in accordance with claim 12, wherein
side marginal portions of said absorbent article are non-elasticized except by any elastication from said spaced apart elastic elements.

16. A disposable absorbent article in accordance with claim 12, wherein
said one of said elastic elements positioned in the lower half of said upstanding portion is spaced throughout its extent from said backsheet.

17. A disposable absorbent article in accordance with claim 12, wherein
said one of said elastic elements is spaced no more than about 0.25 inches from said backsheet.

* * * * *